United States Patent [19]

Sides et al.

[11] Patent Number: 5,014,541

[45] Date of Patent: * May 14, 1991

[54] CONTINUOUS AIR MONITORING APPARATUS AND METHOD

[75] Inventors: Gary D. Sides, Alabaster; Marion Cates, Pinson, both of Ala.

[73] Assignee: CMS Research Corporation, Birmingham, Ala.

[*] Notice: The portion of the term of this patent subsequent to Feb. 21, 2009 has been disclaimed.

[21] Appl. No.: 313,163

[22] Filed: Feb. 21, 1989

Related U.S. Application Data

[63] Continuation-in-part of Ser. No. 158,334, Feb. 22, 1988, Pat. No. 4,805,441.

[51] Int. Cl.$^5$ .............................................. G01N 30/08
[52] U.S. Cl. ........................................ 73/23.41; 422/89
[58] Field of Search ................ 73/23.1; 55/67; 422/89

[56] References Cited

U.S. PATENT DOCUMENTS 3,357,232 12/1967 Lauer ................................ 73/23.1 X
4,805,441 2/1989 Sides et al. ............................ 73/23.1

Primary Examiner—Hezron E. Williams
Assistant Examiner—Joseph W. Roskos
Attorney, Agent, or Firm—Jennings, Carter, Thompson & Veal

[57] ABSTRACT

A continuous air monitoring apparatus utilizes a solid sorbent preconcentrator to concentrate airborne sorbent compounds for gas chromatographic analysis. Direct connection between the preconcentrator and gas chromatographic column allows direct desorption of the compounds into the column with minimal dead space. Temperature control on the column allows sharp chromatographic peaks to be attained without cryogenic focussing.

3 Claims, 4 Drawing Sheets

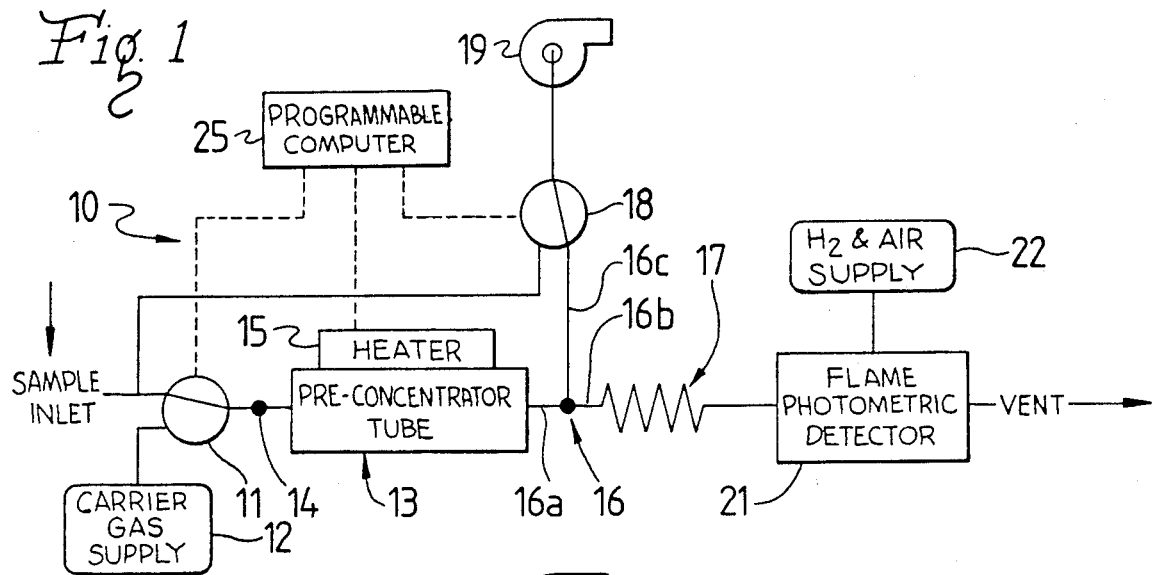
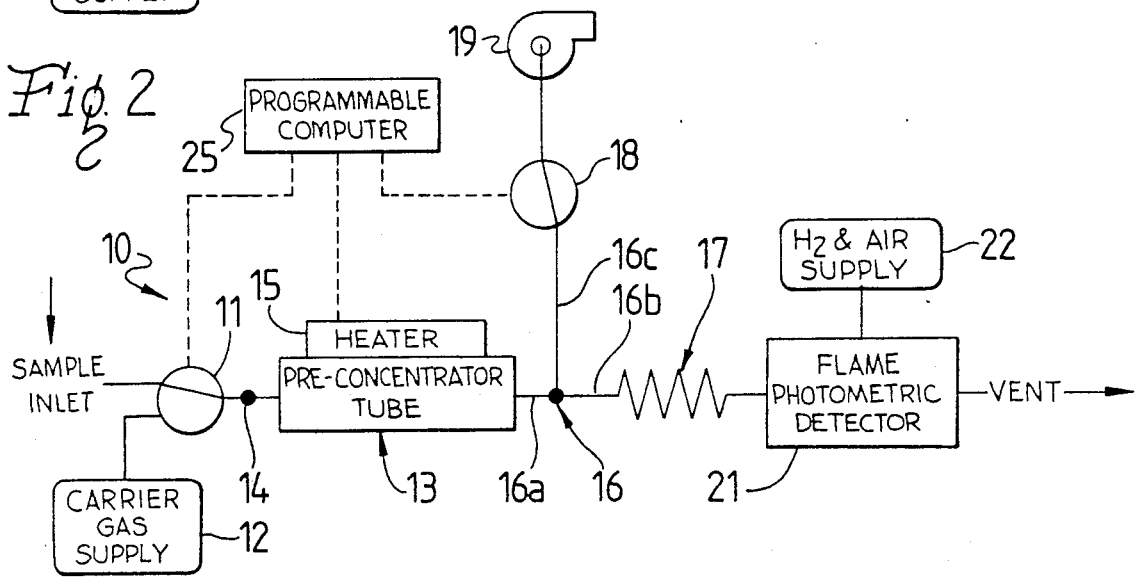
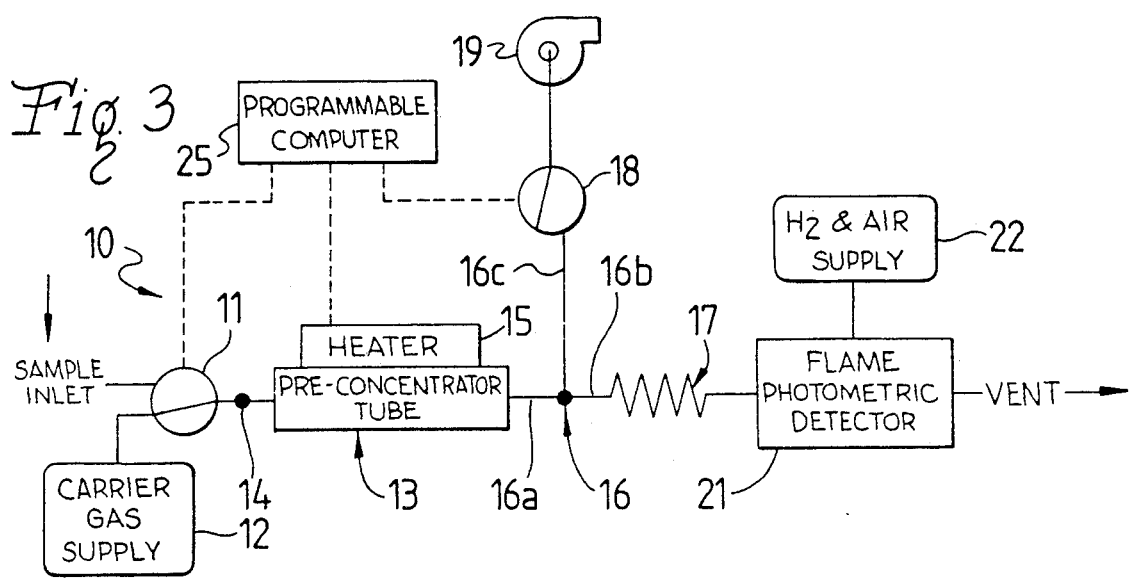

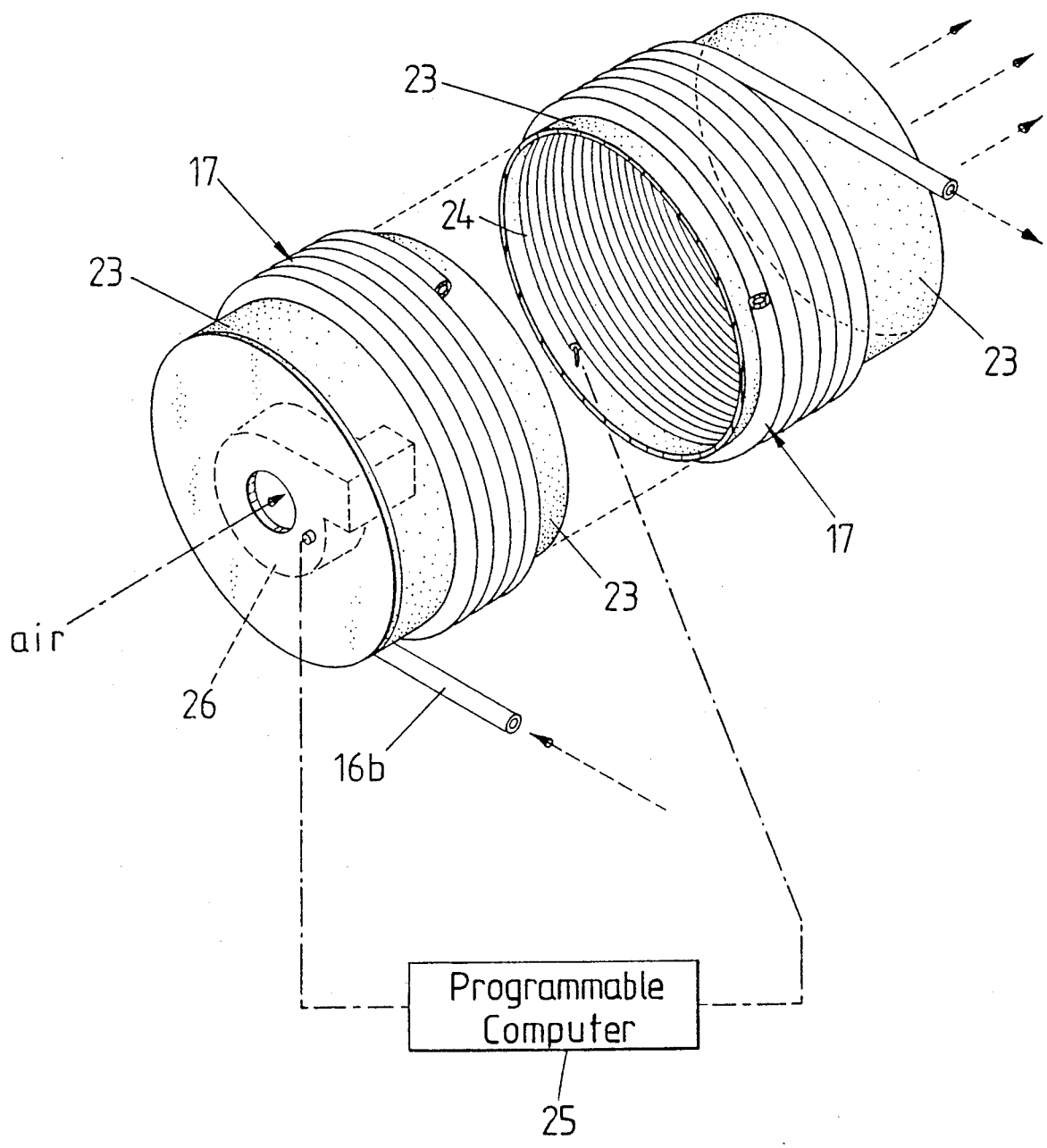

CONTINUOUS AIR MONITORING APPARATUS AND METHOD

This is a continuation-in-part of application Ser. No. 07/158,334, filed Feb. 22, 1988, now U.S. Pat. No. 4,805,441.

FIELD OF THE INVENTION

The present invention relates to gas chromatography and more particularly to apparatus for continuously sampling an air or gas supply and detecting desired compounds in the air or gas. In greater particularity, the present invention relates to solid sorbent sampling/gas chromatographic analysis devices.

BACKGROUND OF THE INVENTION

Gas chromatography has proven to be a reliable and highly useful tool in separating subject compounds from potentially interfering compounds which would otherwise make it difficult to quantify and identify subject compounds in an atmospheric sample. Nonetheless, such compounds are often found in only trace amounts which makes their analysis very difficult. When the compounds are hazardous or lethal, it is imperative that they be detected before a dangerous concentration level is reached. It is known to use a preconcentrator step employing cryogenic trapping and or an adsorbent in order to detect trace amounts of such compounds as organosulfur or organophosphorus compounds. Unfortunately, even with these preconcentrator steps, the detectable quantities of the subject compounds remain above desirable levels. One limiting factor in reducing the detectable quantity has been the internal losses in systems designed to sample and detect trace compounds in the atmosphere.

Exemplary of the problem is U.S. Pat. No. 4,399,688 to Dennis. Dennis recognized that compounds of interest such as air pollutants may react with sample lines or with other components during transport for analysis. Dennis, however, was working with concentrations of 1 part per billion or greater and thus determined that conduit runs of several hundred feet between his concentrator and analyzer were acceptable and that such preconcentration was of no benefit unless the sample site was more than 10 feet from the analyzer. Accordingly, Dennis also determined that any suitable valving system could be used in the concentrator system, and preferenced a diaphragm switching valve. While such devices as Dennis may be suitable for concentrations greater than 1 part per billion, they are unsuitable for use in detecting lower concentrations of certain compounds.

SUMMARY OF THE INVENTION

It is the principal object of the present invention to provide a sampling and analysis system that is capable of determination of chemical compounds at concentrations as low as 10 parts per trillion.

In support of the principal object, another object of the invention is to provide a sampling and analysis system with minimal reactive losses and minimal dead space.

Yet another object of the invention is to provide sharper chromatographic peaks through ambient temperature focussing of the compounds.

Still another object of the invention is to provide sampling and analysis units which can be located in relatively small, remote areas.

A further object of the invention is to provide improved cycling time to allow a greater number of samples to be analyzed in a given time period.

These and other objects and advantages of our invention are accomplished through the use of a solid sorbent preconcentrator connected to a gas chromatographic column with minimal dead space therebetween and no intermediate valving. Thus reactive losses in transit from the preconcentrator to the gas chromatographic column are minimized. Further, sharper chromatographic peaks for lower concentrations are achieved using optimized temperature regimes in desorbing and focussing the compounds into the gas chromatographic column.

BRIEF DESCRIPTION OF THE DRAWINGS

Apparatus embodying features of our invention are depicted in the accompanying drawings which form a portion of this disclosure and wherein:

FIG. 1 is a schematic representation of our sampling and analysis unit in the sample mode;

FIG. 2 is a schematic representation of our unit in the purge mode;

FIG. 3 is a schematic representation of our unit in the analysis mode;

FIG. 4 is a partial perspective view showing our gas chromatographic column assembly;

DESCRIPTION OF A PREFERRED EMBODIMENT

Figure 5:
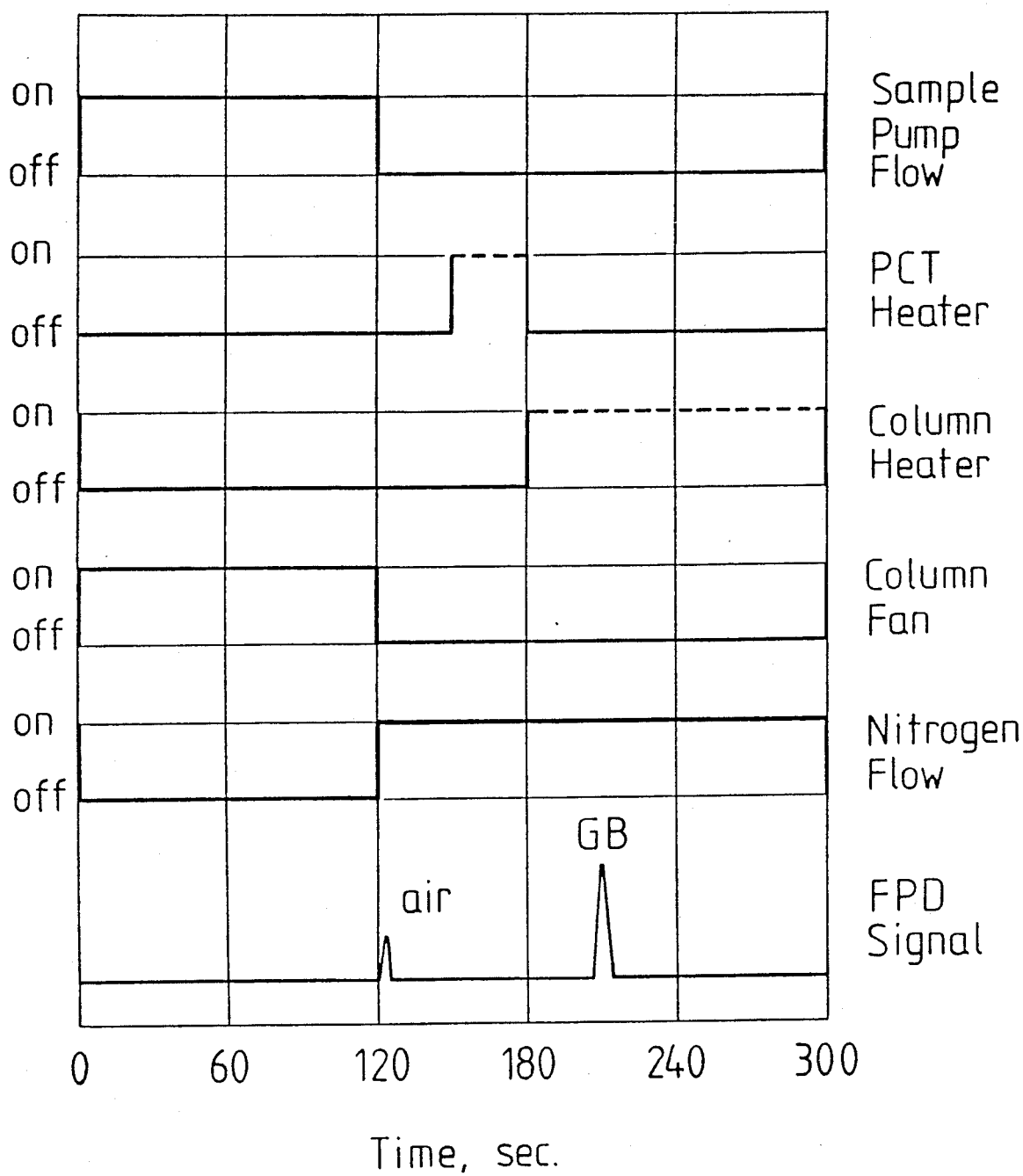
FIG. 5 is a timing diagram for one cycle of the unit's operation.

Referring to the drawings for a clearer understanding of the invention, it should be noted that the present invention contemplates the use of one or more remote monitors which include a gas chromatographic module that accomplishes the sampling and analysis functions. The remote monitor also has an electronics package which serves as an interface between the monitor and a controlling programmable computer 25 located at some distance from the monitor. The electronics package and the computer may assume a variety of structural configurations which are well known in the art that are not germane to the present invention so long as they are capable of exchanging data and control signals with the monitor. Therefore further discussion of the electronics package is omitted in the interest of clarity. The monitor, shown generally at 10 in FIGS. 1-3, weighs about 15 pounds and has a chassis that is about 10 in × 12 in × 6.5 in. The monitor 10 may thus be mounted inside chemical fume hoods or at sites where access to the monitor 10 must be restricted for safety reasons.

One set of parameters upon which gas chromatography separation of compounds depend are the physical parameters under which the compound is applied to the gas chromatographic (GC) column. These physical parameters include the absence of significant dead volume, contamination, and gas leaks. The plumbing shown in FIG. 1-3 is designed to minimize each of these. Referring to the figures, the monitor 10 includes an inlet valve 11 having two inlet ports, one connected to the atmosphere and the other to a source 12 of compressed carrier gas. The valve 11 has an outlet port connected to a solid sorbent preconcentrator tube 13 through a fitting 14. The preconcentrator tube 13 is a thin glass-walled tube packed with a solid sorbent and wrapped with a nichrome wire heater 15. The solid sorbent may be such porous polymers as HayeSep D, Tenax-GC, Chromosorb 106 or any other commercially available sorbent which will collect the desired compounds.

The preconcentrator tube 13 is connected to a junction fitting 16 which includes a T connector. One leg 16a of the T connector is connected to the preconcentrator tube 13 and a second leg 16b is connected to a gas chromatographic (GC) column 17. A third leg 16c connects a venting valve 18 and is intermediate to the preconcentrator tube 13 and the gas chromatographic column 17. The venting valve 18 has one inlet communicating with the junction fitting 16 and may have a second inlet communicating with a sampling inlet proximal the inlet port of the inlet valve 11 as shown in FIG. 1. However, as shown in FIGS. 2 and 3, such sampling communication is not necessary. The outlet of venting valve 18 is connected to a sampling pump 19.

Figure 6:
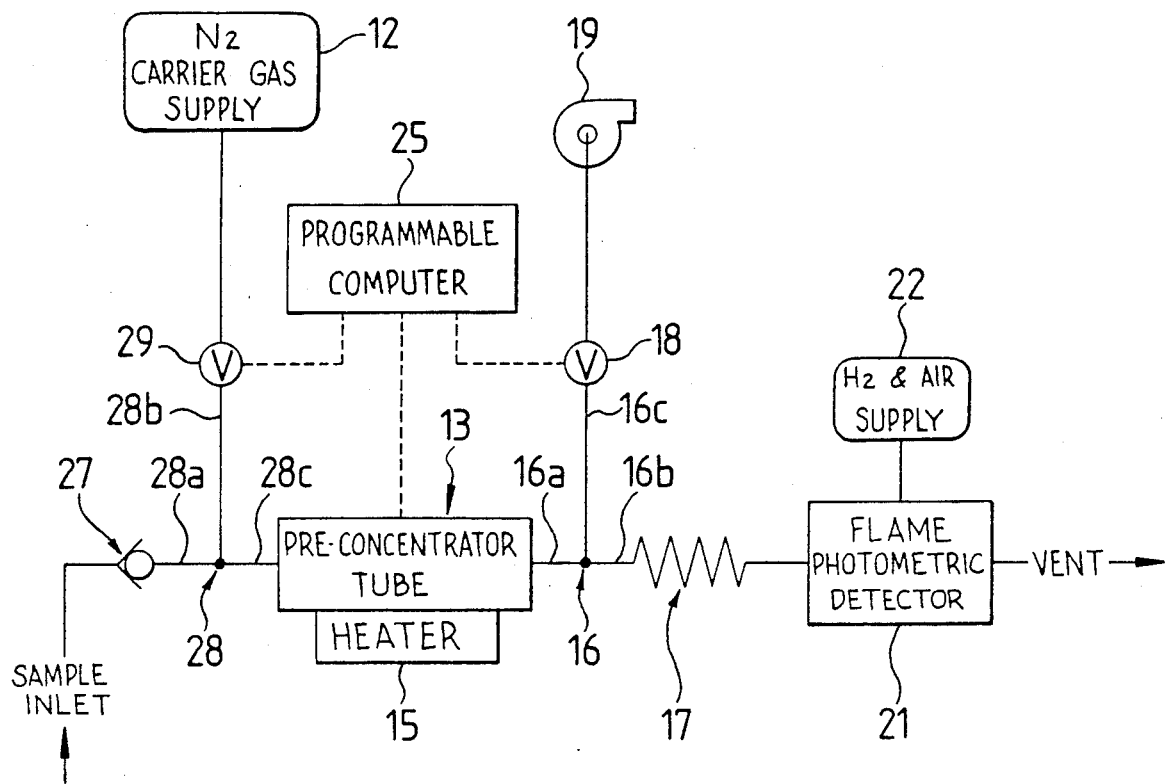
FIG. 6 is an alternate embodiment of our unit.

An alternative to the preceding described system may afford even better sampling. As should be understood, the sensitivity of the sampling is in part determined by the volume of gas passed through the preconcentrator tube 13 in a sampling interval. This volume is limited by the flow rate which in turn is affected by various restrictors in the flow path. Prior art devices and, to some extent, the previously described circuit suffer limitations due to valving restrictions due to the need to beat in line valves. In FIG. 6, we present an arrangement which substantially reduces the restriction on the flow path and which does not require heated fittings in the flow path. In this embodiment the sample inlet is connected to a high capacity check valve 27 which is connected to one leg 28a of a junction fitting 28. A second leg 28b is connected to the carrier gas source 12 through a controllable valve 29 and a third leg 28c is connected to the preconcentrator tube 13. In this arrangement, the check valve 27 does not present a significant restriction nor does it have to be heated during the sampling interval. Likewise venting valve 18 can be sized to avoid undesirable restrictions and is downstream of the preconcentrator tube 13, thus it needs no heating. Valve 29 is used only to admit the carrier gas, thus its restrictions are not a factor in the sampling flow rate.

The gas chromatographic column 17 is connected to a flame photometric detector 21 which is connected to a compressed hydrogen and air gas supply 22 and is vented. The carrier gas supply and hydrogen and air gas supply both include pressure regulators with restrictors which are adjusted to provide proper flow of gases in the system.

The gas chromatographic column 17 is supported on a tubular heat conductor support 23 as illustrated in FIG. 4. The gas chromatographic column 17 is a restrictor of considerable length and thus is wrapped externally about the support 23. A heater element 24 such as a coil or mat is placed proximal the inner surface support to heat the gas chromatographic column 17. A fan 26 is mounted inside the support 23 and is used to cool the gas chromatographic column 17 and heater 24. It may be possible to eliminate the heater 24 entirely by using an electrically resistive gas chromatographic column 17 and passing a current therethrough. In any event the gas chromatographic column 17 must have associated with it a means for rapidly raising its temperature from 50° C. to at least 120° C. within 20 seconds and a means for cooling the gas chromatographic column from about 180° C. to 50° C. within two minutes. The apparatus described hereinabove has been shown to meet these criteria.

The inlet valve 11, venting valve 18, preconcentrator heater 15, gas chromatographic column heater 24, and fan 26 are all controlled by a programmable computer 25 which is programmed to control the sequence of sampling and analysis for selected compounds. The operation of the apparatus may be more clearly understood with reference to FIGS. 1-3 and 5. During sampling, the valves 11 and 18 are set as shown in FIG. 1 so that the sampling pump 19 draws air through the preconcentrator tube 13 where the subject compound and other compounds are captured on the solid sorbent. During sampling the carrier gas (nitrogen or another gas) does not flow through either the preconcentrator tube 13 or the gas chromatographic column 17. After a sufficient quantity of air has passed through the preconcentrator tube 13 to adequately concentrate the subject compound on the solid sorbent, valve 11 is switched to receive carrier gas as shown in FIG. 2. Note that the sampling period may vary depending on the subject compound. The configuration depicted in FIG. 2 allows carrier gas to flow through the preconcentrator tube 13, fitting 16, valve 18, and sample pump 19 to purge the preconcentrator tube 13, thereby reducing oxidation of the solid sorbent and contamination of the sample. When the purge is completed, venting valve 18 is closed, as shown in FIG. 3, so that the pressurized carrier gas flows through the gas chromatographic column 17 which is a thick film gas chromatographic column, that is, a fused silica capillary column. The nichrome wire heater 15 rapidly heats the solid sorbent to 200° C. and maintains this temperature for 20 to 30 seconds desorbing the trapped compounds into the carrier gas flow for transport into the gas chromatographic column 17. Note that once the compounds of interest are collected on the preconcentrator tube (a solid-sorbent bed or precolumn), they do not have to pass through a valve to reach the gas chromatographic column. This allows a very low dead volume between the preconcentrator tube and the gas chromatographic column, which leads to excellent chromatographic performance of the system. Compounds pass through a valve only during the sample period, when the flow rate of gas through the valve is relatively large. Thus, the loss of compounds on surfaces in the sampling system is minimized. The gas chromatographic column 17 is at about 50° C. as the compounds are eluted thereinto, thus the compounds tend to focus in the entry end of the gas chromatographic column. When the compounds have been desorbed into the gas chromatographic column 17, the heater 24 rapidly heats the column from about 50° C. to about 120° C., thereby freeing the compounds from the focussed state for chromatographic separation at temperatures above 120° C.

The compounds pass from the gas chromatographic column 17 to the flame photometric detector 21 where they are incinerated in a hydrogen/air flame. The light from the flame passes through an optical filter to select the wavelength of interest and into a photomultiplier tube to yield an electric current which is converted to a voltage signal which indicates the presence of the detected compound to the programmable computer 25, which can use the signal to initiate further action such as sounding alarms or it can record the data.

When the analysis is completed, the valves 11 and 18 are returned to the FIG. 1 configuration, the gas chromatographic column heater 24 is turned off, the fan 26 is turned on, and the pump 19 draws another sample into the preconcentrator tube 13. Hydrogen may back flush through the gas chromatographic column 17 during the sample period. The cycle may be repeated indefinitely. It is noteworthy to mention that neither the preconcentrator step nor the focussing step of the above cycle requires cryogenic temperatures. Heretofore, focussing techniques have required cooling the gas chromatographic column to −40° C. to freeze the compounds at the gas chromatographic column inlet area. Our method of preconcentration on solid sorbent, at ambient temperatures, followed by rapid desorption into a thick film capillary column, with minimal dead volume, at 50° C. and rapid heating of the column to above 120° C. yields sharp chromatographic peaks for very low concentrations without the need for expensive and space consuming cryogenic equipment. Furthermore, the cycle time of cryogenic units is many times longer than the present invention. From the foregoing, it should be clear that the present apparatus and method represent a substantial improvement over the prior art.

While we have shown our invention in two forms, it will be obvious to those skilled in the art that it is not so limited but is susceptible of various changes and modifications without departing from the spirit thereof.

What we claim is:

1. Apparatus for use in gas chromatography comprising:
   (a) a gas chromatographic column;
   (b) a solid sorbent preconcentrator tube in communication with said gas chromatographic column;
   (c) an inlet check valve connected to said solid sorbent preconcentrator tube to permit a sampling air stream therethrough in one direction and to prevent airflow in opposition to said sampling air stream;
   (d) a reservoir of carrier gas, connected to said solid sorbent preconcentrator tube intermediate said preconcentrator tube and said inlet check valve to selectively pass carrier gas therethrough;
   (e) means for selectively venting said carrier gas intermediate said preconcentrator tube and said gas chromatographic column; and
   (f) means for desorbing sampled material from said preconcentrator tube into said carrier gas.

2. Apparatus as defined in claim 1 further comprises means for backflushing said gas chromatographic column with a gas.

3. Apparatus as defined in claim 1 wherein said means for desorbing includes means for controlling the temperature regime of said solid sorbent preconcentrator tube within predetermined temporal and thermal levels.

* * * * *